US00PP22032P2

(12) United States Plant Patent
Austin

(10) Patent No.: US PP22,032 P2
(45) Date of Patent: Jul. 19, 2011

(54) ***ROSA HYBRIDA* SHRUB NAMED 'AUSJOSIAH'**

(50) Latin Name: *Rosa hybrida shrub*
Varietal Denomination: AUSjosiah

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 12/800,483

(22) Filed: May 17, 2010

(30) Foreign Application Priority Data

Feb. 11, 2010 (GB) ..... AFP 5/2116

(51) Int. Cl.
*A01H 5/00* (2006.01)

(52) U.S. Cl. ..... Plt./107

(58) Field of Classification Search ..... Plt./107
See application file for complete search history.

*Primary Examiner* — Annette Para

(74) *Attorney, Agent, or Firm* — Kauth, Pomeroy, Peck & Bailey LLP

(57) ABSTRACT

A variety of rose plant of the shrub class, named 'AUSjosiah'. The 'AUSjosiah' rose is a plant suitable for repeat flowering production having beautiful and delicate individual blooms of a soft rose pink with a lovely fragrance which is fruity on outer petals with clove in center. The growth is exceptionally vigorous, sending up many shoots from the base and forming a large rampant shrub. The ample foliage is dark green and glossy.

1 Drawing Sheet

Classification: The present invention relates to a new *Rosa hybrida* shrub.

Variety denomination: The new plant has the varietal denomination 'AUSjosiah'.

CROSS-REFERENCE TO RELATED APPLICATIONS

The current application claims priority to a United Kingdom Breeder's Right Certificate Application No. AFP 5/2116, filed Feb. 11, 2010, the disclosure of which is incorporated herein by reference.

ORIGIN OF INVENTION

This invention relates to a new and distinct variety of shrub rose plant named 'AUSjosiah', which was originated by crossing two unnamed, unpatented varieties of *Rosa hybrida*.

BACKGROUND OF THE INVENTION

The primary objective of this breeding was to produce an exceptionally vigorous flowering variety having delicate individual blooms of a soft rose pink with a lovely fragrance, which is fruity on the outer petals and clove in the center.

SUMMARY OF THE INVENTION

Among the features which distinguish the new variety from other presently available and commercial rose cultivars known to the inventor is the following combination of characteristics: beautiful and delicate individual blooms of a soft rose pink with a lovely fragrance which is fruity on the outer petals with clove in the center, exceptionally vigorous growth sending up many shoots from the base and forming a large rampant shrub, and ample foliage that is dark green and glossy.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSjosiah' may be asexually propagated by budding and grafting. The budding and grafting successfully occurred on the plant/rootstock *Rosa* cv. 'Dr. Huey' in the United States and on the plant/rootstock *Rosa dumetorum* cv. 'Laxa' in the United Kingdom.

COMPARISON WITH PARENTS

The new rose may be distinguished from its seed parent, by the following combination of characteristics: whereas the seed parent is not as disease resistant and has larger more open blooms, 'AUSjosiah' bears individual blooms of a soft rose pink with a lovely fragrance which is fruity on the outer petals with clove scents in the center.

The new variety may be distinguished from its pollen parent, by the following combination of characteristics: whereas the pollen parent is an overall poorer quality plant, 'AUSjosiah' is exceptionally vigorous.

COMPARISON WITH THE CLOSEST COMMERCIALLY AVAILABLE CULTIVAR

The closest commercially available cultivar to the new variety is the 'AUSrumba' (U.S. Plant Pat. No. 17,500). The new rose may be distinguished from the 'AUSrumba' variety by the following combination of characteristics: the 'AUSrumba' is a medium height rounded shrub, whereas the 'AUSjosiah' is a vigorous shrub, the 'AUSrumba' produces blooms having a fragrance of strong old rose with a hint of myrrh, compared to 'AUSjosiah', which produces a fruity fragrance with clove. In addition, the bud color of the 'AUSjosiah' is pink, and the buds of 'AUSrumba' are apricot-colored.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 2 year-old rose plants of the new variety grown outdoors in Albrighton, Britain in the month of July. Phenotypic expression may vary with environmental, cultural and climatic conditions, as well as differences in conditions of light and soil.

Flower characteristics:

Blooming habit.—Recurrent. The number of blooms per plant during the growing season is profuse, but there are too many to count.

Bud:

*Size.*—About 3.2 cm long and 2 cm in diameter when the petals start to unfurl.

*Form.*—The bud form is globular.

*Color.*—When sepals first divide, the bud color is pink RHS 69D, with red flecks. When half blown, the upper sides of the petals are pink RHS 68D, and the lower sides of the petals are pink RHS 69D.

*Calyx.*—Shape: (from above) star-shaped. Length: 6 cm. Diameter: 6 cm.

*Sepals.*—Arrangement: Pointing downwards. Color: Upper Surface: green RHS N138D. Lower Surface: green RHS N143A. Length: 3 cm. Width: 1 cm. Shape: Acuminate. Margin: N/A. Surface texture: Upper Surface: Mossy. Lower Surface: Leathery. Number: There are three normally appendaged sepals. There are 2 unappendaged sepals with hairy edges.

*Receptacles.*—Color: green RHS N143A. Shape: pear. Size: medium, about 1.5 cm×1 cm. Surface: Smooth.

*Peduncle.*—Length: medium, averaging about 6.5 cm. Surface: prickly. Color: bronzy RHS 178A. Strength: Strong.

Blooms:

*Size.*—Large, average open diameter is about 9 cm.

*Borne.*—Several together (4-14) blooms having pyramidal shape.

*Stems.*—Strength: Strong, average length is about 5-8 cm. Diameter: 3-4 cm.

*Form.*—When first open, bloom is globular. Permanence of bloom: outer petals curl back.

Petalage: Number of petals under normal conditions: 70.

*Color.*—The upper sides of the petals are salmon pink RHS Group 62D. The reverse sides of the petals are pink RHS 62D. The base of the petals has a spot of RHS 11D, with a small yellow spot RHS 133D on the reverse side.

*Discoloration.*—General tonality at end of first day is salmon pink RHS 62D, and at the end of the third day is pink RHS 36D, and further changes with aging to cream RHS 11D.

*Fragrance.*—Strong. Character of fragrance: Fruity on outer petals with clove in the center.

Petals:

*Texture.*—Smooth.

*Size.*—Width: 30 mm. Length: 40 mm.

*Surface.*—Smooth.

*Shape.*—Round.

*Margin.*—Notched.

*Apex shape.*—Rounded.

*Base shape.*—Pointed.

*Form.*—Incurved.

*Arrangement.*—Irregular.

*Petaloids.*—Number: 19. Color: pink RHS 62D. Length: 30 mm. Width: 20 mm. Shape: Narrow elliptical. Margin: Medium undulating, medium reflexing.

*Persistence.*—Petals hang on and dry.

*Lastingness.*—On the plant: fair, about 4 days. As a cut flower: not tested.

Reproductive parts:

*Stamens.*—Number: 65. Length: 13 mm.

*Anthers.*—Length: 3 mm. Color: yellow-orange RHS 22A. Arrangement: Regular around styles.

*Filaments.*—Color: red RHS 44B. Length: 10 mm.

*Pollen.*—Color: yellow-orange RHS 22A.

*Pistils.*—Number: 30. Length: 6 mm.

*Styles.*—Color: red RHS 44B with yellow RHS 22A. Length: 3 mm.

*Stigmas.*—Color: red RHS 44B with yellow RHS 22A. Length: 3 mm.

*Hips.*—None Observed.

PLANT CHARACTERISTICS

Plant form: Large Shrub (Would train as climber).

Plant growth: Very vigorous.

Age to maturity: Two years.

Mature plant: Height: 1.5 m. Width: 1.5 m.

Rootstock: *Rosa* 'Dr. Huey for U.S. and *Rosa dumetorum* cv. 'Laxa' for observed plants in the U.K.

Foliage:

*Number.*—Leaflets on normal mid-stem leaves is: 5-7 (including terminal leaflet).

*Size.*—Large, about 16 cm long×12 cm wide.

*Quantity.*—Abundant. Number of leaves per flowering stem is: 12.

*Color.*—New foliage: Upper side: bronze (grey-brown) RHS N199A. Lower side: bronze (grey-orange) RHS 166A. Old foliage: Upper side: dark green RHS 139A. Lower side: green RHS 144A.

Leaflets:

*Size.*—About 5 cm long×3.5 cm wide.

*Shape.*—Pointed Oval.

*Base shape.*—Cordate.

*Apex shape.*—Obtuse.

*Texture.*—Glossy.

*Edge.*—Serrated.

*Serrations.*—Single.

*Petiole.*—Color: green RHS 147C. Length: 3.5 cm. Width: 2 mm. Surface Texture: With prickles.

*Petiole rachis.*—Color: green RHS 147C. Underside: with prickles.

*Stipules.*—Length: 1-2 cm, bearded. Color: green RHS 144A.

*Auricle.*—Shape: Pointed. Length: 1 cm. Width: 1 mm. Color: green RHS 144A.

*Vein color.*—Green RHS 139B.

*Venation pattern.*—Pinnate.

Wood:

*New wood.*—Color: brown-red RHS 178A. Bark: Rough.

*Old wood.*—Color: brown-red RHS 178A and yellow-green RHS N144D. Bark: Rough.

Branching habit:

*Number.*—5 per main stem.

*Lateral branch dimensions: Length:* 15 cm. Diameter: 0.5-1 cm.

Stems:

*Mature stem.*—Length: 25-30 cm. Diameter: 1 cm.

*Internode distance.*—30 mm. The above measurements are all variable, depending on growing conditions in a season.

*Stem pubescence present.*—Yes.

Prickles:

*Quantity.*—On main canes from base: ordinary. Number per stem length: 6 per 10 cm. On laterals from main canes: many. Number per stem length: 12 per 10 cm.

*Form.*—Deep concave.

*Length.*—8 mm.

*Color when young.*—Red RHS 183A.

*Color when mature.*—Red RHS 186A.

Small prickles:

*Quantity.*—Main stalk: few. Number per stem length: 2 per 10 cm. Laterals: Many.

*Color.*—When young: red RHS 183A. When mature: red RHS N186A.

Disease resistance:

*Mildew.*—Resistant.

*Blackspot.*—Resistant.

*Rust.*—Resistant.

Pest resistance: Not tested.

Winter hardiness: Not tested.

Growing conditions: Normal.

What is claimed is:

1. A new and distinct variety of rose plant of the shrub class suitable for repeat flower production, substantially as herein shown and described.

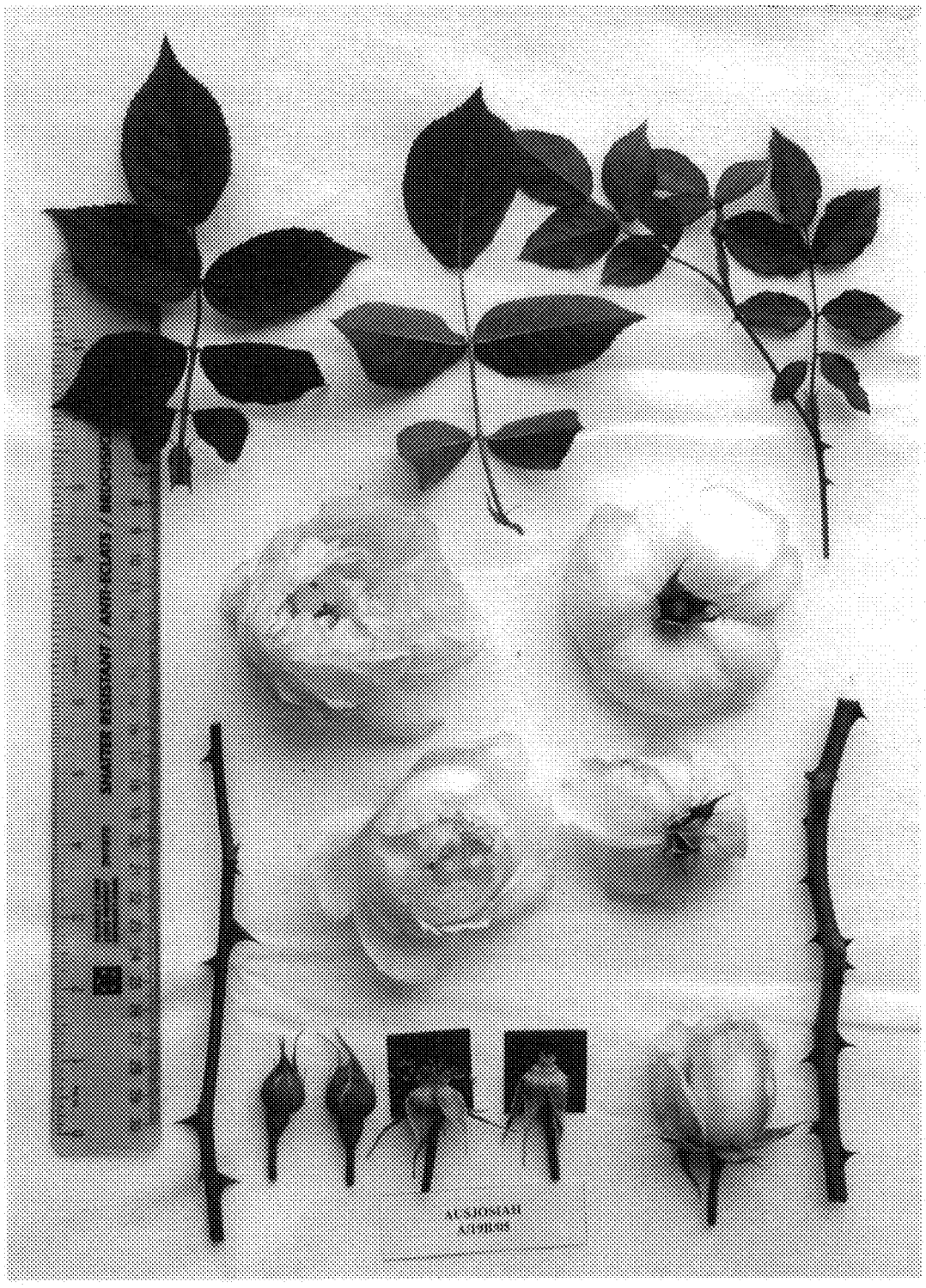

* * * * *